US006392124B1

(12) United States Patent
Ponz Ascaso et al.

(10) Patent No.: US 6,392,124 B1
(45) Date of Patent: May 21, 2002

(54) INFECTIOUS VECTORS AND CLONES OF PLANTS DERIVED FROM THE TURNIP MOSAIC VIRUS (TUMV)

(75) Inventors: Fernando Ponz Ascaso; Vicente Torres Pascual; Florentina Sanchez Sanchez, all of Madrid; David Martinez Herrera, Pozuelo de Alarcon, all of (ES)

(73) Assignee: Institute Nacional de Investigacion Y Tecnologia Agraria Y Alimentaria (INIA), Madrid (ES)

( * ) Notice: Subject to any disclaimer, the term of this patent is extended or adjusted under 35 U.S.C. 154(b) by 0 days.

(21) Appl. No.: 09/462,569
(22) PCT Filed: Sep. 7, 1999
(86) PCT No.: PCT/ES98/00200

§ 371 Date: Apr. 3, 2000

§ 102(e) Date: Apr. 3, 2000

(87) PCT Pub. No.: WO99/02718

PCT Pub. Date: Jan. 21, 1999

(30) Foreign Application Priority Data

Jul. 9, 1997 (ES) .............................................. 9701522

(51) Int. Cl.[7] ........................ C12N 15/83; C12N 15/70; C12N 15/40; A01H 5/00

(52) U.S. Cl. ...................... 800/288; 800/306; 435/91.4; 435/91.32; 435/468; 536/23.72

(58) Field of Search ................................ 800/278, 288, 800/306; 435/320.1, 91.4, 91.32, 468; 536/23.72

(56) References Cited

FOREIGN PATENT DOCUMENTS

| | | |
|---|---|---|
| EP | 0693555 | 1/1996 |
| WO | WO9512669 | 5/1995 |

OTHER PUBLICATIONS

Flasinski et al., The cDNA sequence and infectious transcripts of peanut virus, 1996, Gene, vol. 171, pp. 299–300.*
Jenner et al., The cylindrical inclusion gene of turnip mosaic virus encodes a pathogenic determinant to the brassica resistance gene TuRB01, 2000, Molecular Plant–Microbe Interactions, vol. 13, No. 10, pp. 1102–1108.*

Sanchez et al., Infectivity of turnip mosaic potyvirus cDNA clones and transcripts on the systemic host *Arabidopsis thaliana* and local lesion hosts, 1998, Virus Research, vol. 55, pp. 207–219.*

Chu–Hui Chiang et al., "Infectivity Assays of in vitro and in vivo Transcripts of Papaya Ringspot Potyvirus," Bot. Bull. Acad. Sin. 38:153–163 (1997).

Ling–Jie Kong et al., "Turnip Mosaic Virus Coat Protein Gene: Cloning and Construction of the Plant Vector," Science in China (Series B) 35(12):1444–1452 (Dec. 1992).

Olivier Nicolas et al., "The Use of PCR for Cloning of Large cDNA Fragments of Turnip Mosaic Potyvirus," Journal of Virological Methods 32:57–66 (1991).

Olivier Nicolas et al., "The Complete Nucleotide Sequence of Turnip Mosaic Potyvirus RNA," Journal of General Virology 73:2785–2793 (1992).

K. Ohshima et al., "The Complete Nucleotide Sequence of Turnip Mosaic Virus RNA Japanese Strain," Arch. Virol. 141:1991–1997 (1996).

Marie–Francine Tremblay et al., "Sequence of the 3'–Terminal Region of Turnip Mosaic Virus RNA and the Capsid Protein Gene," Journal of General Virology 71:2769–2772 (1990).

* cited by examiner

*Primary Examiner*—Scott D. Priebe
*Assistant Examiner*—Eleanor Sorbello
(74) *Attorney, Agent, or Firm*—Ostrolenk, Faber, Gerb & Soffen, LLP

(57) ABSTRACT

The infectious clone comprises: a) a complete copy of the complementary DNA (cDNA) to the genomic RNA of the turnip mosaic virus (TuMV), in the form of double stranded DNA, b) a transcription promoter sequence, c) a replicon and, optionally, d) a transcription termination or polyadenilation sequence. Viral vectors comprise an infectious clone modified to contain a gene or a heterologous gene fragment. Infectious viral clones and vectors are useful for basic research, in virology and for the expression of genes and epitopes of interest.

11 Claims, 3 Drawing Sheets

Figure 1A:
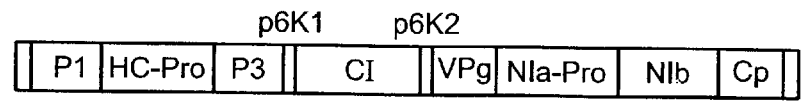
Figure 1B:
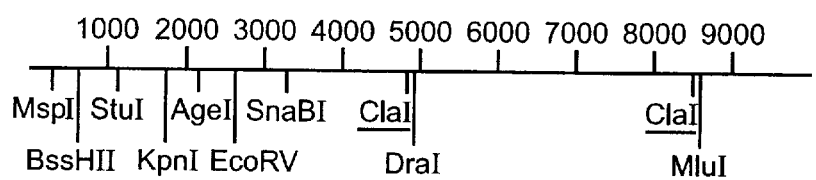
Figure 1C:
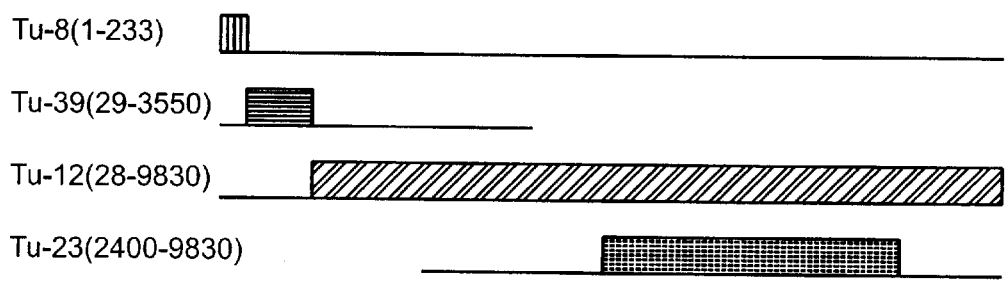
Figure 1D:
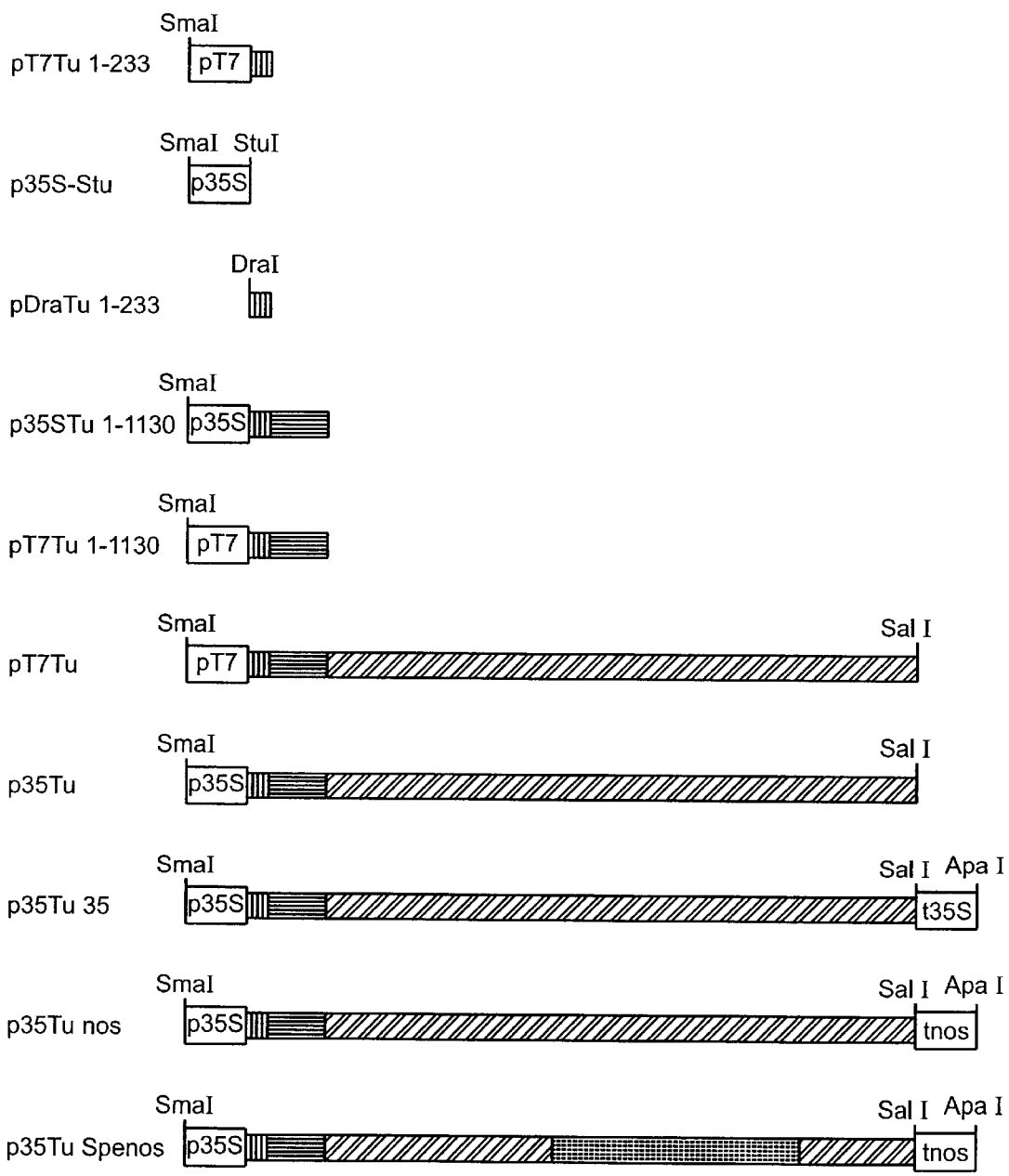
Figure 1E:
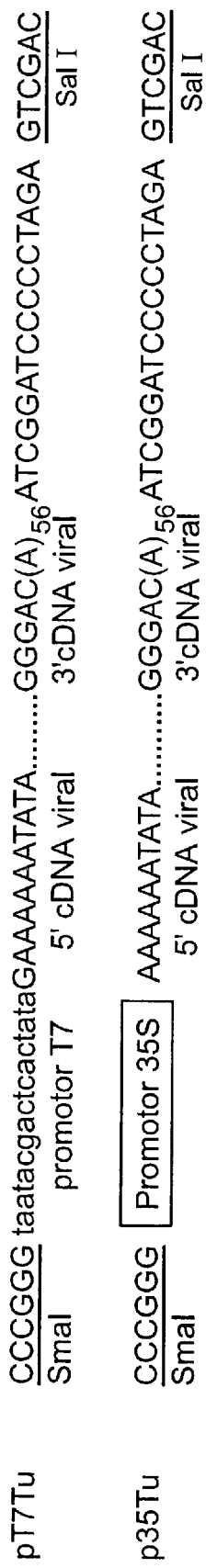

INFECTIOUS VECTORS AND CLONES OF PLANTS DERIVED FROM THE TURNIP MOSAIC VIRUS (TUMV)

SCOPE OF THE INVENTION

The invention refers to infective clones of the turnip mosaic virus (TuMV) and to plant infectious viral vectors based on said infectious clones.

BACKGROUND OF THE INVENTION

Infectious viral clones comprise a DNA molecule and some transcription regulating mechanisms, capable of synthesising a transcript which can infect plants of plant cells (protoplasts). Infectious clones, in themselves, constitute a very valuable tool in basic research in Virology and, besides, are the necessary starting element for the preparation of plant viral vectors.

Plant viruses show different types of genoma: single stranded DNA (for example, geminivirus), double stranded DNA (for example, pararetrovirus), positive polarity RNA, i.e., messenger direction (for example potyvirus), negative polarity RNA (for instance rabdovirus), double polarity RNA (for instance tospovirus) or double stranded RNA (for instance reovirus). Recombinant DNA technology initially allowed the development of infectious clones of plant viruses with DNA genoma (geminivirus and pararetrovirus). Afterwards, thanks to the development of reverse transcriptases infectious clones have been obtained from numerous plant virus groups with positive polarity RNA genoma [Boyer, J. C. & Haenni, A. L. (1994). Infectious transcripts and cDNA clones of RNA viruses. *Virology*, 198, 415–426]. Infectious clones from the following potyviruses have been described:

- Sharka virus (PPV) [Maiss E., Timple U., Brisske Rode A., Lesemann D. E. & Casper R. (1992). Infectious in vivo transcripts of a plum pox potyvirus full length cDNA clone containing the cauliflower mosaic virus 35S RNA promoter. *Journal of General Virology*, 73, 709–712; Riechmann J. L., Lain S. & Garcia J. A. (1990). Infectious in vitro transcripts from a plum box potyvirus cDNA clone. *Virology*, 177, 710–126];
- Tobacco vein mottling virus (TVMV) [Domier L. L., Franklin K. M., Hunt A. G., Thoads R. E. & Shaw J. G. (1989). Infectious in vitro transcripts from cloned cDNA of a potyvirus, tobacco vein mottling virus. *Proceedings of the National Academy of Sciences USA*, 86, 3509–3513];
- Tobacco engraving virus (TEV) [Doija V. V., McBride H. J. & Carrington J. C. (1992). Tagging of plant potyvirus replication and movement by insertion of □-glucuronidase into the viral polyprotein. *Proceedings of the National Academy of Sciences USA*, 89, 10208–10212];
- Pea seedborne mosaic virus (PSbMV) [Johansen I. E., Dougherty W. G., Keller K. E., Wang D. & Hampton R. O. (1996). Multiple viral determinants affect seed transmission of pea seedborne mosaic virus in Pisum sativum. *Journal of General Virology*, 77, 3149–3154];
- Peanut stripe virus (PStV) [Flasinki S., Gunasinghe U. B., Gonzales R. A. & Cassidy B. G. (1996). The cDNA sequence and infectious transcripts of peanut stripe virus. *Gene*, 171, 299–300];
- Zucchini yellow mosaic virus (ZYMV) [Gal-On A., Antignus Y., Rosner A. & Raccah B. (1991). Infectious in vitro RNA transcripts derived from cloned cDNA of the cucurbit potyvirus, zucchini yellow mosaic virus, *Journal of General Virology*, 72, 2639–2643; Galon A., Meiri E., Huet H., Hua W. J., Raccah B. & Gaba V. (1995). Particle bombardment drastically increases the infectivity of cloned DNA of zucchini yellow mosaic potyvirus, *Journal of General Virology*, 76, 3223–3227];
- Papaya ringspot potyvirus (PRSV) [Chiang C. H. & Yeh S. D. (1995). Construction of infectious in vitro transcripts of papaya ringspot potyvirus. 6$^{th}$ International Plant Virus Epidemiology Symposium, Ma'ale Hachamisha, Jerusalem, Israel, page 52]; and
- Potato A virus (PVA) [Puurand V., Valkonen J., Makinen K., Rabenstein F. & Saarma M. (1996). Infectious in vitro transcripts form cloned cDNA of the potato A potyvirus. *Virus Research*, 40, 135–140.

The genoma of most of the plant viruses comprises one or several positive polarity RNA molecules. The infectious clones of plant viruses with RNA genoma basically comprise a complementary DNA (cDNA) to the viral genomic RNA and a promoter sequence linked to said cDNA. This promoter sequence can either be that of a bacteriophage, which allows the obtaining of viral RNA by in vitro transcription by the corresponding RNA polymerase, or else that of A plant functional gene, which allows, after the introduction of the DNA into the plants, in vivo production of the corresponding effective viral RNA.

The obtaining of an full length infectious clone from an RNA template (the viral genoma of an RNA virus) implies, in the first place, the use of a reverse transcriptase in order to make a first cDNA chain, in the second place, the synthesis of double stranded cDNA by means of a DNA polymerase, and, in the third place, the linking of different cDNA restriction fragments, although this third stage is not always carried out because some full length infectious clones have been prepared by means of the polymerase (RT-PCR) reserve transcription—chain reaction. The obtaining of a full length infectious clone from an RNA template is a complicated procedure which shows many difficulties since (i) a reading error in the polymerases may take place during either of the first two stages, and (ii) errors may also occur in the linking of the restriction fragments either by the presence of exonucleases or else by the presence of restriction fragments, small and difficult to detect, for the enzyme being used, entailing both kinds of errors the obtaining of full length clones which are not infectious [Boyer, J. C. & Haenni, A. L. (1994). Infectious transcripts and cDNA clones of RNA viruses. *Virology*, 198, 415–426]. Another factor which also has an influence is the precision of the linking of the promoter to the cDNA. The infectivity is very much decreased, even with 5' extensions of 1 or 2 nucleotides, however, the 3' extensions do not have such a big influence in the biological activity [Boyer, J. C. & Haenni, A. L. (1994). Infectious transcripts and cDNA clones of RNA viruses. *Virology*, 198, 415–426]. On the other hand, the handling of full length viruses is very complex due to the unstableness problems which they show.

One of the main applications for plant infectious viral clones is their use in the construction of viral vectors. A plant infectious viral vector consists, in general, of a infectious viral clone modified in such a way that it contains a heterologous nucleic acid sequence which is expressed after inoculating plants or plant cells with said vector.

Plant viral vectors are used to research molecular biology processes in plants and are useful as tools in order to study plant viral infections processes. Besides, plant viral vectors have been developed in order to substitute and/or insert genes and to show epitopes. Among the commercial applications of known plant viral vectors are the expression of the interpheron alphaD gene, the expression of alpha-tricosanthine (inhibitor of viral replication in the human immunodeffiency virus [HIV]), the expression of the peptide inhibiting the enzyme which converts angiotensine I, the presentation of epitopes of the flu virus, of HIV-1, of malaria epitopes, and the expression of antigenic peptides of the glosopeda virus and human rhinovirus 14 (Scholthof, H. B., Scholthof, K. B. G. & Jackson, A. O. (1996). Plant virus gene vectors for transient expression of foreign proteins in plants. *Annual Review of Phytopathology*, 34, 299–323]. On the other hand, plant infectious vectors represent an alternative to the obtaining of transgenic plants and show numerous advantages, among which are, for instance, high expression in a short period of time, the expression of genes which can make more difficult the regeneration or the growth of transgenic plants and the possibility of a transient expression.

Plant viruses have a limited and specific range of hosts. Most of the plant species are not infected by most viruses, i.e., each virus is capable of infecting a unique combination of plant species [Dawson, W. O. & Hilf, M. E. (1992. Host range determinants of plant viruses. *Annual Review of Plant Physiology and Plant Molecular Biology*, 43, 527–555]. This situation implies that, with the present knowledge level of the factors determining the host range, it is impossible to obtain universal plant viral vectors. Therefore, there exists the need of looking for new clones and plant infectious viral vectors which can be used to infect useful plants as models for the study of the expression of heterologous and epitope genes of pathogens. The invention provides some turnip mosaic virus infectious clones, as well as some viral vectors based on said infectious vectors, adequate for infecting plants of *Arabidopsis thaliana* (L.) Heynh.

The turnip mosaic virus, hereinafter TuMV (Turnip mosaic virus) belongs to the potyvirus family, which are flexuous viruses whose virons are made of only one positive polarity RNA molecule of approximately 10,000 nucleotides, and of approximately 2,000 copies of only one type of protein, the coat protein (CP). The RNA genoma has a 5' area and another 3' one which are not translated (of approximately 150 and 200 bases respectively) constituting the central part of only one open reading stage which, when is translated, gives rise to only one polyprotein which is processed by means of at least 3 proteases coded by the virus in 8–10-gene products. [Riechmann J. L., Lain S. & Garcia J. A. (1992). Highlights and prospects of potyvirus molecular biology. *Journal of General Virology*, 73, 1–16]. The full sequence of a Canadian isolate of TuMV has been published [Nicolas, O. & Laliberte, J. F. (1992). The complete nucleotide sequence of turnip mosaic potyvirus RNA. *Journal of General Virology*, 73, 2785–2793] as well as that of a Japanese isolate [Oshima K., Tanaka M. & Sako N. (1996). The complete nucleotide sequence of turnip mosaic virus RNA Japanese strain. *Archives of Virology*, 141, 1991–1997].

BRIEF DESCRIPTION OF THE FIGURES

FIG. 1 shows:

the genome organisation of TuMV, where the different genes are shown [P1: protein 1; HC-Pro: helper component protease; P3: protein 3; p6K1: 6 kilodalton peptide 1; CI: cylindrical inclusion: p6K2:6 kilodalton peptide 2; VPg: viral protein genome linked; Nia-Pro: small nuclear inclusion protein-protease; NIb; large nuclear Inclusion protein; Cp: coat protein] (FIG. 1A);

the scale (in nucleotides), the restriction map for unique cut points and the enzymes used in the construction of infectious clones [MspI, in bold, has not been mapped throughout the genome, and ClaT, underlined, has two cutting sites] (FIG. 1B);

the clones of cDNA or of RACE-PCR used in the construction of the infectious clones [the name of the clone is followed by positions 5' and 3' of the cDNA insert in parenthesis; the horizontal line indicates the area of he genome represented by the clone and the box with the weft represents the area of the clone used in the construction of infectious clone (FIG. 1C);

infectious clones and intermediate clones in their construction (the sequences corresponding to the T7 and 35S promoter and to the nos and 35S terminators are indicated by boxes and their corresponding name (FIG. 1D); and details at the nucleotic sequence level in the full length nucleotides, at the linking areas of cDNA to the promoters (5' end) or at the 3' end. The arrow points to the transcription initiation. The promoter T7 is shown at the nucleotide level. The 35S promoter is shown in a box (FIG. 1E).

DETAILED DESCRIPTION OF THE INVENTION

This invention relates to an infectious clone of the turnip mosaic virus (TuMV), which comprises:

a full copy of complementary DNA (cDNA) to the genomic RNA of TuMV, in the shape of a double stranded DNA;

a transcription promoter sequence; and a replicon.

In a particular embodiment, the TuMV is the UK1 isolate, and the full copy (cDNA) contains a poly-A tail at the 3' end.

The transcription promoter sequence or promoter, is a DNA sequence located at the 5'-terminal end and immediately before nucleotide (nt) 1 of the cDNA of the genomic RNA, onto which the RNA polymerase binds in order to initiate the transcription of messenger RNA (mRNA). Said promoter is chosen from:

i) an adequate promoter for the in vitro transcription of cDNA by means of the corresponding RNA polymerase, such as a bacteriophage promoter, for instance, T3, T7 SP6 or lambda Pm, and, if so be the case, one or more nucleotides in order to allow an optimal transcription of the full length cDNA, for instance, an additional G in case the promoter used is T7 and the cDNA does not start with a G; and ii) a promoter of a plant functional gene, adequate for the in vivo transcription of infectious viral RNA, for instance, the 35S promoter of the cauliflower mosaic virus (CaMV), and a transcription termination sequence or one signalling polyadenilation, for instance, the terminator of the nopaline sinthetase gene (nos) of the Ti plasmid of *Agrobacterium tumefaciens* or the polyadenilation signal of the 35S gene of CaMV. These termination sequences must be located at the 3' end of the poly(A) tail. Sometimes, there may be a variable number of nucleotides between the last nucleotide on the 3' end of the poly(A) tail and the first nucleotide of the transcription termination sequence or of the polyadenilation signal.

The replicon is a DNA molecule which has a replication origin and is, therefore, potentially capable of replicating inside of an adequate cell. An example of a replicon is a plasmid. The replicon is adequate for the maintenance and amplification of the infectious clone inside of an adequate host cell, such as a bacterial host, for instance, *Escherichia coli* (*E. Coli*). The replicon generally carries an antibiotic resistance gene which allows the selection and avoids the loss of the replicon as such or as a chimera after the insertion of the above mentioned elements. In a particular embodiment, the replicon is a plasmid chosen from pUC12 and pUC13.

Example 1 describes the construction of three infectious clones of the UK1 isolate of the TuMV virus. The three of them have the same full length sequence, cDNA, of the genome of TuMV UK1. One of the clones is adequate for the inoculation with RNA, since the cDNA is under the control of the promoter of the bacteriophage T7, while the other two clones are adequate for the DNA inoculation, they have the same promoter, promoter 35S of CaMV, but one of them has the CaMV 35S polyadenilation signal and the other one the nos terminator gene.

The procedure for the obtaining of said infectious clones entails the construction of cDNA, full length, of the genomic RNA of the potyvirus and the assemblage of transcription regulating elements (promoters and, if so be the case, terminators).

In a particular embodiment (cf. Examples 1.1. and 1.2), the full length cDNA of the genomic RNA of TuMV, has been constructed by means of the linking of three different fragments:

a) a fragment of approximately 8.7 kilobases (kb) coming from a cDNA from TuMV UK1 of 9.8 kb obtained by standard synthesis of cDNA used as (3') reverse primer a d(T)36 oligo identified as SEQ. ID. NO.: 4 (cf. the LIST OF SEQUENCES);

b) a fragment of 900 nt, internal to a clone of cDNA of 3.55 kb of TuMV UK1 obtained by the standard synthesis of cDNA using as (3') reverse primer an oligonucleotide complementary to nt 4769–4747 of the Canadian TuMV isolate, identified as SEQ. ID. NO.: 2; and c) the first 200 nt, generated by means of RT-PCR, with a specific (3') reverse primer complementary to the 233–212 positions of the TuMV UK1 genoma, called Tu 233–212 and identified as SEQ. ID. NO.: 3, and a (5') direct primer from a commercial kit (5' ampli-FINDER RACE kit, Clontech).

These fragments have been linked, in the manner indicated in the examples, in order to get the full length cDNA of the viral genomic RNA.

In the sense used in this description, the expression "standard cDNA synthesis" refers to synthesis by means of reverse transcriptase and the second chain by means of the action of RNasaH and DNA polymerase.

Some of the elements or sequences used for the construction of the infectious clones provided by this invention are products known and available in the market, such as the replicon (plasmids pUC13 and pUC12), the T7 promoter sequence, the CaMV 35S promoter sequences and the polyadenilation signal (from a commercial plasmid, by PCR amplification by specially designed primers) and the sequence of the nos gene terminator (by means of the amplification by PCR of a commercial plasmid with specially designed primers).

TuMV infectious clones provided by this invention are adequate for basic research in Virology and for the construction of plant viral vectors.

An additional subject matter of this invention relates to a recombinant viral vector derived from a TuMV infectious clone provided by this invention. Said viral vector comprises a RuMV infectious clone modified in order to contain a gene or a heterologous gene fragment in said infectious clone under conditions which allow the expression of said gene or gene fragment after the infection of a plant or a protoplast by said recombinant viral vector.

Heterologous genes or fragments which the viral vectors provided by this invention may contain, may comprise any gene or fragment which codes for a protein, a peptide, an epitope or any gene product of interest. Said genes or heterologous fragments can be introduced into the infectious clone by genetic engineering techniques. It is essential in the construction of viral vectors, that the introduction of the heterologous gene or fragment does not interfere with any of the basic viral functions. A very interesting application of plant infectious viral vectors is the expression in plants of animal viral epitopes in order to produce edible vaccines against said animal viruses.

The invention also provides a method to infect plants which entails the putting together of one of the TuMV infectious clones provided by this invention or a viral infectious vector derived from said clone with a plant susceptible of being infected by TuMV. In a particular embodiment, the viral clone or vector derives from the TuMV UK1 isolate and the plant belongs to the *Arabidopsis thaliana* (L.) Heynh species.

The following Examples serve the purpose of illustrating the invention and should not be considered as limiting of the scope of the same.

EXAMPLE 1

Infectious Clone Construction 1.1 Obtaining of cDNA from TuMV

The TuMV isolate used is isolate TuMV UK1, donated by Dr. J. Walsh (HRI, Wellesbourne, United Kingdom). The TuMV UK1 isolate was purified from Indian mustard plants (*Brassica juncea*) inoculated with said virus three weeks before harvesting. The RNA extracted from the virus was used as the template for the synthesis of cDNA. Said synthesis was carried out, basically, according to the protocol described in the Amersham kit (cDNA synthesis module kit), with some modifications. Reverse transcriptase superscript RNaseH⁻ (Gibco-BRL) was used for the synthesis of the first chain, using as primers those identified as SEQ. ID. NO.: 1 [cf. the SEQUENCE LIST] which corresponds to a d(T)14 oligo and as SEQ. ID. NO: 2, an oligonucleotide complementary to the nucleotide sequence 4769–4747 of Canadian TuMV isolate. The cDNA fragments where cloned into pUC13 [Messing, J. (1983). New M13 vectors for cloning. *Methods in Enzymology*, 100 B, 20–78] digested with SmaI and treated with phosphatases (shrimp alkaline phosphatase, USB]. Clones were analysed by restriction with different endonucleases and by determination of the sequence at the ends. The position of the nucleotides corresponding to the viral genoma were assigned to the ends of the inserts, by similarity to the sequence of the complete genome of another TuMV isolate [Nicolas, O. & Laliberté, J. F. (1992). The complete nucleotide sequence of turnip mosaic potyvirus RNA. *Journal of General Virology*, 73, 2785–2793]. Two clones were selected (Tu-23 2400–9830 and Tu-39 29–3550) which contain overlapping inserts which represent the almost full length cDNA of TuMV UK1, except for the 28 first nucleotides of the 5' end.

The cDNA corresponding to the 233 nt of the 5' end was synthesised by PCR using an oligonucleotide complementary to positions 233–212 of the UK1 genoma (Tu 233–212) as the primer; identified as SEQ. ID. NO.: 3 and the (5')

direct primer ampliFINDER RACE (Clontech) under the following conditions:

number of cycles: 35
temperature/time: 45 seconds (s) at 94° C.
45 s at 60° C., and
2 minutes at 72° C.

The PCR fragments were cloned, after blunting the ends with T4 DNA polymerase and introducing a phosphate at 5' by means of the T4 polynucleotide kinase. The sequence of the 5' viral end was determined from said clones and also directly from the viral RNA using the oligonucleotide identified as SEQ. ID. NO.: 3 and the RT RNA sequencing kit (USB) as primers. The sequence of the ten clones was completely coincident except that they showed length heterogeneity at the 5' end (4, 5 or 6 As). A clone was selected, named Tu-8, which had 6 As at the 5' end.

1.2 cDNA Synthesised with a d(T) 36 Oligo Primer

The analysis of the preceding cDNA clones indicated the presence of some short poly (A) tails (of approximately 14 nt) at the 3' end. A cDNA was synthesised using for the primer in the synthesis of the first chain the primer known as SEQ. ID. NO.: 4, a d(T)36 oligo (New England Biolabs), and said cDNA was cloned into a modified pUC13 vector which contained the following multiple cloning site:

HindIII-PstI-SalI-KpnI-EcoRV-BamHI-SmaI-SacI-EcoRI, digested with EcoRV and treated with phosphatase. The analysis of the clones thus obtained indicated the presence of a variable length (9–56 nt) poly(A) tail. Among these clones was a clone named Tu-12, with an insert size of about 9.8 kilobases (kb) approximately and a poly(A) tail of 56 residues, and said clone covered the genome of TuMV UK1 from nucleotide 28.

1.3. Restriction Map of cDNA

In order to determine the restriction map of the full length cDNA (by overlapping of the restriction maps of the Tu-8, Tu-39 and Tu-23 clones) of TuMV UK1, the following enzymes were used: AflII, AgeI, BamHI, BssHII, ClaI, DraI, Eco47III, EcoRI, EcoRV, HindIII, HpaI, KpnI, MluI, NruI, NsiI, PstI, SacI, SnaBI, SpeI, StuI, XbaI, XhoI. No cutting sites have been detected for the following enzymes: AccIII, ApaI, EagI, NcoI, GgoMI, NotI, SalI, SmaI, SacII.

Table 1 shows the number of cutting sites and the approximate location in the cDNA derived from the TuMV genoma of the cutting sites for the restriction enzymes assayed.

TABLE 1

| Enzyme | No. | Site |
|---|---|---|
| AflII | 3 | 2500, 3700, 5700 |
| AgeI | 1 | 2100 |
| BamHI | 2 | 2600, 6100 |
| BssHII | 1 | 600 |
| ClaI | 2 | 4700, 8400 |
| DraI | 1 | 4900 |
| Eco47III | 2 | 3100, 8600 |
| EcoRI | 5 | 1100, 1700, 5300, 8300, 9300 |
| EcoRV | 1 | 2550 |
| HindIII | 3 | 2600, 3800, 5800 |
| HpaI | 2 | 1000, 8500 |
| KpnI | 1 | 1900 |
| MluI | 1 | 8600 |
| NruI | 2 | 1300, 5300 |
| NsiI | 3 | 2100, 5100, 9600 |
| PstI | 2 | 5500, 6100 |
| SacI | 2 | 5700, 7900 |
| SnaBI | 1 | 3300 |
| SpeI | 5–6* | 2440, 2900, 3300, 3800, 6900, 7100* |
| StuI | 1 | 1130 |
| XbaI | 4 | 2800, 4900, 5300, 8500 |
| XhoI | 4 | 1800, 3700, 5600, 8400 |

*the cutting site SpeI at the 7100 position is only present in certain cDNA clones, and absent (or minoritarious) in the viral population (in the viral genoma).

1.4 Fusion of the 35S Promoter to the viral cDNA

The 35S promoter [432 base pairs (pb)] of the CaMV was amplified by PCR using the pRT101 plasmid as the template [Töpfer, R., Matzeit, V., Gronenborn, B., Schell, J., and Steinbiss, H. H. (1987). A set of plant expression vectors for transcriptional and translational fusions. Nucleic Acids Research, 15 (14): 5890], as the (5') direct primer, the one identified as SEQ. ID. NO: 5 and as the (3') reverse primer the one identified as SEQ. ID. NO.: 6, under the following conditions: heating to 94° C. for 5 minutes and then 30 30 s. cycles at 94° C, 1 minute at 62° C. and 5 minutes at 72° C.

The amplified fragment was treated with T4 DNA polymerase, was phosphorilated with T4 polynucleotide kinase, was digested with BamHI, was subjected to electrophoresis in polyacrilamide gel (PAA) with 5% TBE (Tris 0.089 M, Borate 0.089 M, EDTA 0.002 M), was purified from the gel [Sambrook J., Fritsch E. F. & Maniatis T. (1989). Molecular cloning: A laboratory manual. Cold Spring Harbor Laboratory Press, New York;

Smith H. O. (1980). Recovery of DNA from gels. Methods in Enzymology 65, 371–380], and was cloned into the pUC13 vector digested with SmaI-BamHI. The primers were designed in order for the fragment to have a SmaI site at the 5' end and a StuI site right before the transcription initiation site, following the general strategy normally used to fuse the CaMV 35S promoter (p35S) to the first viral nucleotide [Ding, S. W., Rathjen, J. P., Li, W. X., Swanson, R. Healy, H. & Symons, R. H. (1995). Efficient infection in a new plasmid vector. Journal of General Virology, 76, 459–464; Yamaya, J., Yoshioka, M. Meshi, T. Okada, Y. & Ohno, T. (1988). Expression of tobacco mosaic virus RNA in transgenic plants. *Molecular & General Genetics*, 211, 520–525]. The new plasmid was called p35S.Stu.

The cDNA from TuMV UK1 present in the Tu-8 plasmid was amplified by PCR using the primers identified as (i) SEQ. ID. NO.: 7, a 25 base oligonucleotide (Dra-Tul-22) of which, the first three nucleotides at the 5' end are three additional nucleotides meant to create a DraI restriction site, and the 22 nucleotides left correspond to the first 22 nucleotides at the 5' end of the TuMV UK1 cDNA and (ii) SEQ. ID. NO.: 3. The conditions were the following: 94° C. for 5 minutes; 5 30 s. cycles at 94° C., 30 s at 42° C. and 30 s at 72° C., and 35 30 s cycles at 94° C. and 45 s at 60° C. The amplified fragment (236 pb) was treated with the T4 DNA polymerase, was phosphorilated with T4 polynucleotide kinase, was purified from PAA and was cloned into pUC13 digested with SmaI and dephophorilated with alkaline phosphatase. One clone, the one named pDra Tul-233 was selected after checking that it had the adequate insert.

The DraI-MspI (191 pb) fragment of the pDra-Tul-233 clone and the MspI-MspI (939 pb) fragment of the Tu-39 clone were linked to p35S-StuI, digested with StuI and treated with phosphatase. From this cloning, the p35s Tu 1–1130 clone was selected, which contains the cDNA from TuMV UK1 from nucleotide 1 to 1130 under the control of the promoter 35S. Low yield was detected in the purification of this plasmid; the cloning of the SacI-HindIII fragment from this plasmid at pUC12 gave as result the plasmid p35S Tu 1–1130 (+) (+ indicates that the TuMV gene and the beta-gal insert have the same transcription direction), which showed less yield problems.

1.5 Fusion of the T7 Promoter to the Viral cDNA

The T7 promoter was fused to the first nucleotide of the cDNA of TuMV UK1 by means of the PCR amplification of the fragment present at the Tu-8 clone using the primers identified as (i) SEQ. ID. NO.: 3 and (ii) SEQ. ID. NO.: 8, named T7-Tul-22, a 43 base oligonucleotide of which the first three at the 5' end are used to reconstruct a SmaI site, the 17 following ones for the sequence corresponding to the T7 promoter and the additional G to include a good transcription initiation residue, and the 22 nucleotides left correspond to the first 22 nucleotides of the 5' sequence of the cDNA of UK1. The conditions were the following: 94° C. for 5 minutes; 5 30 s. cycles at 94° C., 30 s at 42° C. and 30 s at 72° C., and 35 30 s cycles at 94° C. and 45 s at 60° C. The amplified fragment (254 pb) was treated with the T4 DNA polymerase, was purified from PAA, was phosphorilated with T4 polynucleotide kinase and was cloned into pUC13 digested with SmaI and treated with phosphatase. One clone, the one named pT7-Tul-233 was selected, containing the adequate sequence. From the pT7-Tul-233 clone the fragment pT7 Tul-191 (SmaI-7MspI ends) was extracted, from the clone Tu-39 the fragment Tu 191–1130 (MspI-StuI ends), and these fragments were linked to the vector fragment (which does not contain the p35S). From this ligate the plasmid pT7 Tu 1–1130 plasmid was selected. Low yield was also detected in the purification of this plasmid; the cloning of the SacI-HindIII fragment of this plasmid into pUC12 gave as a result the plasmid pT7 Tul-1130 (+) (+ indicates that the TuMV insert and the beta-gal gene have the same transcription direction), which showed less yield problems.

1.6 Fusion of the Terminators

The transcription terminators of the (tnos) gene and the polyadenilation signal of 35S (t35S) were obtained by PCR from commercial plasmid templates (see below). In both cases the primers were designed in order that, after the cloning at HindIII, they had a SalI cutting site at the 5' end and ApaI and XhoI sites at the 3' end.

In the case of the 35S polyadenilation signal of the CaMV, the template used was the pRT101 plasmid [Töpfer, R. Matzeit, V., Gronenborn, B., Schell, J., & Steinbiss (1987). A set of plant expression vectors for transcriptional and translational fusions. *Nucleic Acids Research*, 15 5890] and the primers used were those identified as (i) SEQ. ID. NO.: 9, a direct 22 base primer and (ii) SEQ. ID. NO.: 10, a reverse 30 base primer. The amplified fragment had 205 pb.

For the nos gene terminator (tnos), the template was the plasmid pBI2221 (Clontech) and the primers those identified as (i) SEQ. ID. NO.: 11 a 28 base oligonucleotide (direct primer) and (ii) SEQ. ID. NO.: 12, a 29 base oligonucleotide (reverse primer). The amplified fragment had 265 pb.

The amplification reaction in both cases was carried out under the following conditions: 3 minutes at 95° C.; 35 30 s cycles at 95° C., 30 s at 52 ° C. and 1 minute at 72° C.; and finally 5 minutes at 72° C.

The amplified fragments were treated with T4 DNA polymerase, were phosphorilated with T4 polynucleotide kinase, were purified from PAA, and were cloned into pUC13 digested with HincII and treated with phosphatase. The clones pt35S and ptnos were identified which contained the correct fragments.

1.7 Assemblage of the Full Length Clone Under the Control of p35S

The plasmid p35S Tul-1130 (+) [Example 1.4] was digested with XbaI, the 5' sticky ends were blunted by treating with the Klenow fragment of the DNA polymerase of *Escherichia coli*, was then cleaved with StuI and was dephosphorilated with alkaline phosphatase. This vector was ligated to the StuI-SmaI fragment of the Tu-12 clone (8.7 kp, nt 1130–9830 of cDNA from TuMV UK1). From this ligation, the clone named p35 Tu was selected, which contains the full length cDNA from TuMV UK1 under the control of promoter 35S.

1.8 Assemblage of the Full Length Clone Under the Control of pT7

The SmaI-BssHII fragment of the p35 Tu plasmid (containing p35S and cDNA from TuMV UK1 nt 1–600) was substituted by a SmaI-BssHII fragment of the pT7 Tu 1–1130 plasmid. From the resulting construction the plasmid called pT7 Tu was selected which contains the full length cDNA from the genoma of TuMV UK1 under the control of the T7 bacteriophage promoter.

1.9 Introduction of the p35 Tu Terminators

The fragments which contained the terminator of the gene nos (tnos) or the polyadenilation signal of 35S (t35S) were cleaved from the ptnos or pt35S plasmids [Example 1.6] by means of the double SalI-XhoI digestion, were purified from PAA, and were ligated to the p35 Tu plasmid digested with SalI and treated with phosphatase. From these ligations the clones p35 Tu 35 and p35 Tu nos were selected. These clones contained the same full length sequence, cDNA, of the TuMV UK1 genoma, as well as the same promoter, 35S, whilst one of them, p35 Tu 35, contained the t35S one and the other contained the tnos one.

From the p35 Tu nos clone, the p35 Tu Spe nos clone was obtained by substituting a ClaI fragment of p35 Tu nos by the Tu-23 equivalent fragment.

1.10 Stability Test of the Clones

This Example was carried out in order to check the stability of the infectious previously prepared clones of TuMV [see Examples 1.8 and 1.9] since, as it is known, the infectious full length clones of potyvirus are difficult to handle.

In the case of the full length clones previously prepared, both the one which is under the control of the T7 promoter and those under the control of the 35S promoter of CaMV, behave as unstable plasmids in *Escherichia coli* DH5 alpha isolate when they are grown at the optimal growing temperature for *E. coli* (37° C.). This unstableness implies the loss, in a high percentage of the bacterial population, of the plasmid when the carrier isolate of said plasmid is cultured in a rich liquid medium, (in the presence of selective pressure for the plasmid, i.e., ampicillin). In the solid media cultures in the presence of selective pressure (ampicillin), the unstableness implies the appearance of bacterial colonies with a different morphology (irregular edges, yellowish colour) from the one initially shown (smooth edges, translucent); these colonies different in morphology do not contain plasmids or else it is not of the adequate size. The described unstableness in the liquid and solid media disappears when the cultures are carried out at a temperature of 28–32° C.

EXAMPLE 2

Plant Infection Test

This Example was carried out in order to check the infection of plants using either an in vitro or in vivo transcript of TuMV through the usual techniques for plant inoculation.

For the performance of this test *Arabidopsis thaliana* (L.) Heynh RLD ecotype plants were used. The following were used as inoculum:

purified DNA solutions derived from the p35 Tu and p35 Tu nos plasmids [Example 1.9], with a concentration of 0.6 to 2 mg/ml, obtained after the alkaline lysis of a 250 ml culture in LB media (Sambrook J., Fritsch E. F., & Maniatis T. (1989). Molecular cloning: A laboratory manual. Cold Spring Harbor Laboratory Press, New York, grown at 30° C., treated with RNase, phenol and resuspended in TE buffer (10 mM Tris-HCl, 1 mM, pH 9.0 EDTA); and an in vivo transcript RNA solution using the plasmid T7 made linear by SalI as template and a commercial in vitro transcription kit (T7 cap scribe, from Boehringer and mMessage mMachine from Ambion). The transcription was carried out in a 360 µl volume, with 20 µg of template plasmid (pT7 Tu) purified by CsCl and digested with SalI.

As infection controls TE pH 8.0 buffer and purified virus (TuMV) diluted to a concentration of 100 µg/ml in 50 mM pH 7.5 phosphate buffer were used.

In order to carry out this test, the seeds were sterilised, and were sown onto GM media plates (Valvekens D., van Montagu M. & van Lijsebettens M. (1988, *Agrobacterium tumefaciens*- mediated transformation of *Arabidopsis thaliana* root explants by using kanamycin selection. Proceedings of the *National Academy of Sciences USA*, 85, 5536–5540) and were vernalised for 24 hours at 4° C. Then, they were moved to an in vitro culture chamber (16 hour photoperiod, 100 □E m$^{-2}$ s light intensity for 15 days). Once this period of time had elapsed they were transplanted onto soil (universal soil [Floragard] and vermicultite 3:1) and were kept in the culture chamber in the same light conditions and at a temperature of 22° C.

Then, the plants were sprayed with an abrasive, such as silicon carbide. Two leaves of each plant were inoculated with the previously mentioned inoculums (purified DNA derived from p35 Tu 35 and p35 Tu nos plasmids and in vitro RNA transcript solutions). In every case the DNA or RNA solutions were soaked onto a cotton wad and were rubbed onto the leaves to be inoculated.

The results of the different experiments (at least 2 different experiment for each type of inoculum) are indicated in Table 2.

TABLE 2

| Inoculum | Infected plants/inoculated plants | Infection percentage |
| --- | --- | --- |
| Virus | 16/16 | 100 |
| Buffer | 0/16 | 0 |
| RNA transcript + "cap" like structure linear pT7 Tu template | 3/56 | 3 |
| p35 Tu 35 DNA | 6/36 | 16 |
| p35 Tu nos DNA | 13/35 | 37 |

Alternatively, this test could have been carried out by inoculating plant protoplasts with transcript RNA in vitro or with DNA [Leiser, R. M., Ziegler-Graff, V., Reutenauer, A., Herrbach, E., Lemaine, O., Guilley, H., Richards, K. & Jonard, G. (1992). Agro infection as an alternative to insects for infecting plants with beet western yellows luteovirus. *Proceedings of the National Academy of Sciences of the United States of America*, 89, 9136–9140].

MICRO-ORGANISM DEPOSITORY

*Escherichia coli* K12 DH5 alpha strands carriers of the pT7 Tu and p35 Tu nos plasmids have been deposited at the *Collection Espaniola de Cultivos Tipo* (CECT), Burjasot, Valencia (Espana), on 19$^{th}$ December 1996, being assigned access numbers CECT 4822 and CECT 4823 respectively.

What is claimed is:

1. A DNA construct comprising a replicon which comprises:
   a complete copy of complementary DNA (cDNA) to the genomic RNA of turnip mosaic virus (TuMV), in the form of double stranded DNA; and
   a transcription promoter sequence operably linked to said cDNA, said promoter sequence selected from the group consisting of a cauliflower mosaic virus (CaMV) 35S promoter and a T7 RNA polymerase promoter.

2. The DNA construct according to claim 1, which also comprises a transcription termination sequence selected from the group consisting of a nopaline synthase (nos) termination signal and a CaMV 35S polyadenylation signal wherein said transcription termination sequence is operably linked to said cDNA.

3. The DNA construct according to claim 1, wherein said rep wherein said replicon is which is in a plasmid capable of replicating inside of a host *Escherichia coli* bacterial cell.

4. The DNA construct according to claim 1, which comprises the full length cDNA corresponding to the genome of TuMV UK1 under the control of the promoter of the T7 bacteriophage.

5. The DNA construct according to claim 1, which comprises the full length cDNA of the genome of TuMV UK1 under the control of the 35 S promoter of CaMV.

6. The DNA construct according to claim 5, which also comprises the 35S polyadenylation signal of CaMV.

7. The DNA construct according to claim 5, which also comprises the terminator of the nos gene.

8. A procedure for the obtaining of the DNA construct according to claim 1 which comprises the construction of the full length complementary DNA (cDNA) of the genomic RNA of TuMV and the assemblage with the transcription promoter sequences.

9. A recombinant viral vector which comprises a DNA construct according to claim 1 and an heterologous DNA sequence.

10. A method for infecting plants which comprises putting in contact a DNA construct according to claim 1 with a plant susceptible of being infected by TuMV.

11. A method according to claim 10, in which said plant belongs to the *Arabidopsis thaliana* (L.) Heynh species.

* * * * *

UNITED STATES PATENT AND TRADEMARK OFFICE
CERTIFICATE OF CORRECTION

PATENT NO. : 6,392,124 B1
DATED : May 21, 2002
INVENTOR(S) : Ponz Ascaso et al.

It is certified that error appears in the above-identified patent and that said Letters Patent is hereby corrected as shown below:

<u>Title page,</u>
Item [73], change the Assignee to -- Instituto Nacional de Investigacion Y Tecnologia Agraria Y Alimentaria (INIA), Madrid (ES) --.
Item [22], change the PCT Filing Date to -- Jul. 9, 1998 --.

Signed and Sealed this

Thirty-first Day of December, 2002

JAMES E. ROGAN
*Director of the United States Patent and Trademark Office*

SEQUENCE LISTING

<160> NUMBER OF SEQ ID NOS: 12

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: synthetic construct

<400> SEQUENCE: 1 ttttttttttt tttt                                                                                14

<210> SEQ ID NO 2
<211> LENGTH: 22
<212> TYPE: DNA
<213> ORGANISM: Artificial Sequence

```
<220> FEATURE:
<223> OTHER INFORMATION: Description of Artificial  Sequence: synthetic
      construct

<400> SEQUENCE: 2
accacatcaa tgtctagggt ga                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 3
cgcaatggca ttggtgggaa ac                                              22

<210> SEQ ID NO 4
<211> LENGTH: 36
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 4
tttttttttt tttttttttt tttttttttt tttttt                               36

<210> SEQ ID NO 5
<211> LENGTH: 25
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 5
gggaacatgg tggagcacga cacgc                                           25

<210> SEQ ID NO 6
<211> LENGTH: 34
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 6
ccggatccta ggcctctcca aatgaaatga actt                                 34

<210> SEQ ID NO 7
<211> LENGTH: 25
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 7
tttaaaaaat ataaaaactc aacat                                           25

<210> SEQ ID NO 8
<211> LENGTH: 43
<212> TYPE: DNA
<213> ORGANISM: Artificial Sequence
<220> FEATURE:
```

```
<223> OTHER INFORMATION: Description of Artificial  Sequence: synthetic
      construct

<400> SEQUENCE: 8
gggtaatacg actcactata gaaaaaatat aaaaactcaa cat                    43

<210> SEQ ID NO 9
<211> LENGTH: 22
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 9
gacgcaaatc accagtctct ct                                           22

<210> SEQ ID NO 10
<211> LENGTH: 30
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 10
tcgagggccc actggatttt ggttttagga                                   30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 11
gacgatctag taacatagat gacaccgc                                     28

<210> SEQ ID NO 12
<211> LENGTH: 29
<212> TYPE: DNA
<213> ORGANISM: Artificial Sequence
<220> FEATURE:
<223> OTHER INFORMATION: Description of Artificial  Sequence: synthetic
      construct

<400> SEQUENCE: 12
tcgagggccc gatcgttcaa acatttggc                                    29
```